US012672960B2

(12) United States Patent
Huang

(10) Patent No.: US 12,672,960 B2
(45) Date of Patent: Jul. 7, 2026

(54) VALVE REPAIR SYSTEM FOR IMPLANTING ARTIFICIAL CHORDAE TENDINEAE

(71) Applicant: Halocinch Medical Technology (Shenzhen) Co., Ltd, Shenzhen (CN)

(72) Inventor: Hui Huang, Shenzhen (CN)

(73) Assignee: Halocinch Medical Technology (Shenzhen) Co., Ltd, Shenzhen (CN)

( * ) Notice: Subject to any disclaimer, the term of this patent is extended or adjusted under 35 U.S.C. 154(b) by 375 days.

(21) Appl. No.: 18/444,877

(22) Filed: Feb. 19, 2024

(65) Prior Publication Data

US 2024/0189106 A1     Jun. 13, 2024

Related U.S. Application Data

(63) Continuation-in-part of application No. PCT/CN2022/113960, filed on Aug. 22, 2022.

(30) Foreign Application Priority Data

Aug. 24, 2021    (CN) .......................... 202110976242.4

(51) Int. Cl.
| | |
|---|---|
| *A61F 2/24* | (2006.01) |
| *A61B 17/04* | (2006.01) |
| *A61B 17/34* | (2006.01) |
| *A61B 34/00* | (2016.01) |
| *A61B 17/00* | (2006.01) |

(Continued)

(52) U.S. Cl.
CPC ........ *A61F 2/2457* (2013.01); *A61B 17/0469* (2013.01); *A61B 17/3478* (2013.01); *A61B*

*34/76* (2016.02); *A61F 2/2466* (2013.01); *A61B 2017/00473* (2013.01);

(Continued)

(58) Field of Classification Search
CPC .................... A61B 17/0487; A61B 2017/0488
See application file for complete search history.

(56) References Cited

U.S. PATENT DOCUMENTS 10,543,090 B2 * 1/2020 Griswold ........... A61B 17/0469
12,447,011 B2 * 10/2025 Peterson ............... A61F 2/2436
(Continued)

*Primary Examiner* — Jayanti K Patel
(74) *Attorney, Agent, or Firm* — ScienBiziP, P.C.

(57) ABSTRACT

The present application discloses a valve repair system for implanting artificial chordae tendineae, including a handle operation device, a valve clamping device, a valve puncturing device, a catheter, and a grasping-feedback device. The valve clamping device includes a clamping-control component, a proximal clamp, and a distal clamp. The valve puncturing device includes a pulling loop, a connecting component, a puncture needle, and a puncture hollow tube sleeved on the puncture needle. The puncture hollow tube is detachably connected to the connecting component. The pulling loop and the connecting component are received in the distal clamp. The handle operation device includes a handle, a puncturing-operation mechanism, a clamping operating mechanism, and a feedback-operation mechanism. The puncturing-operation mechanism is connected to the puncture needle assembly. The feedback-operation mechanism is connected to the grasping-feedback device. The system has minimal puncture damage and can implant multiple sets of artificial chordae tendineae at a time.

19 Claims, 6 Drawing Sheets

(51) Int. Cl.
　　*A61B 17/29*　　　(2006.01)
　　*A61B 90/00*　　　(2016.01)

(52) U.S. Cl.
　　CPC ............... *A61B 2017/00862* (2013.01); *A61B*
　　　　　　　*2017/2944* (2013.01); *A61B 2090/034*
　　　　　　　　　　　　　　　　　　　(2016.02)

(56)　　　　　　　　References Cited

U.S. PATENT DOCUMENTS

| | | | |
|---|---|---|---|
| 12,447,019 B2 * | 10/2025 | Phan ....................... | A61F 2/246 |
| 12,588,997 B2 * | 3/2026 | Delgado ............... | A61F 2/2454 |
| 2011/0288635 A1 * | 11/2011 | Miller ................... | A61F 2/2457 |
| | | | 606/228 |
| 2016/0038280 A1 * | 2/2016 | Morriss ................ | A61F 2/2436 |
| | | | 623/2.18 |
| 2018/0185150 A1 * | 7/2018 | Bishop .................. | A61F 2/2457 |
| 2019/0183648 A1 * | 6/2019 | Trapp .................... | A61F 2/2466 |
| 2019/0321171 A1 * | 10/2019 | Morriss ................ | A61F 2/2436 |
| 2021/0000599 A1 * | 1/2021 | Shuey .................. | A61F 2/2457 |

* cited by examiner

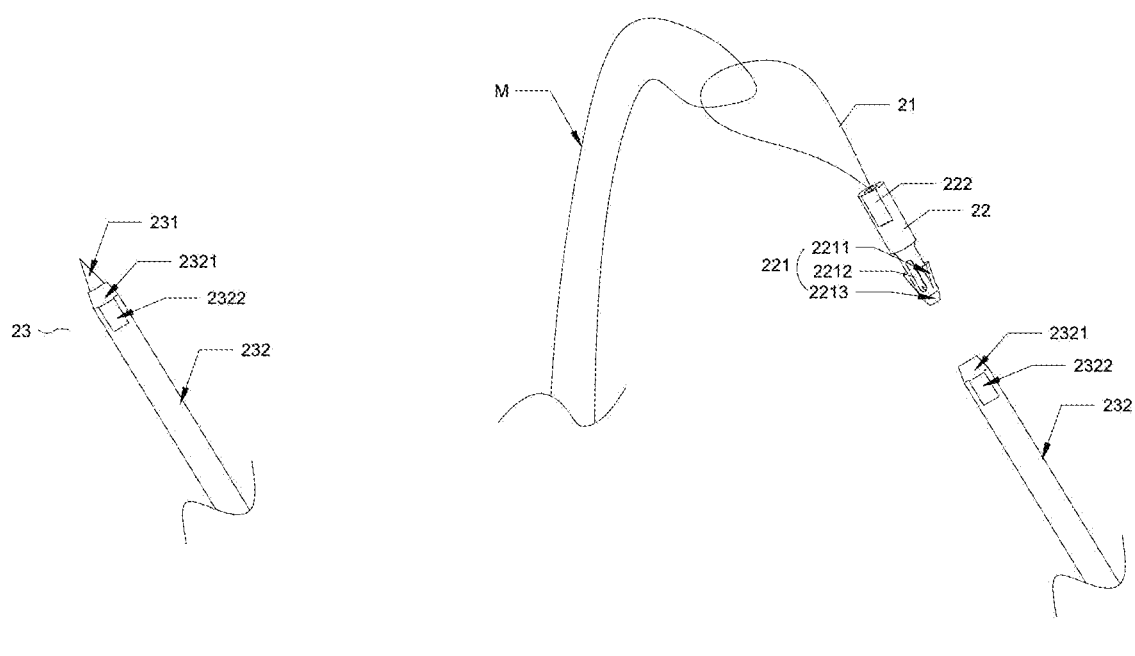
FIG.  5                                        FIG. 6
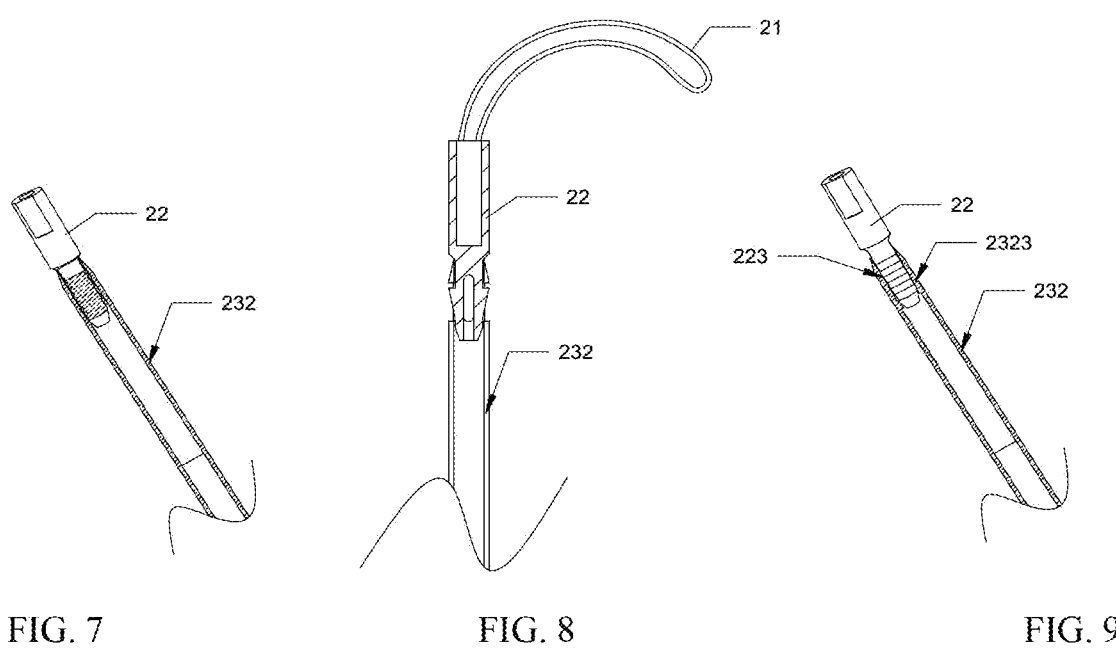
FIG. 7                        FIG. 8                        FIG. 9

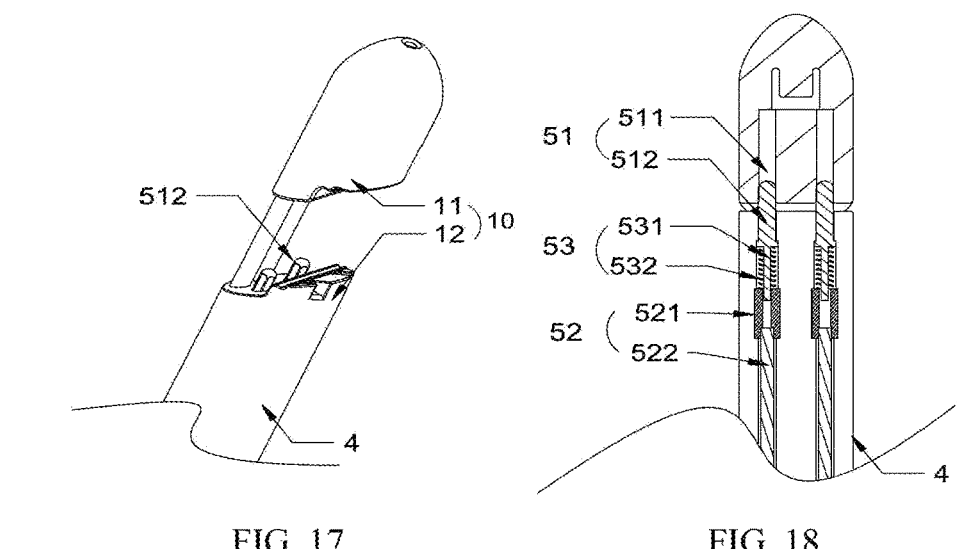
FIG. 17
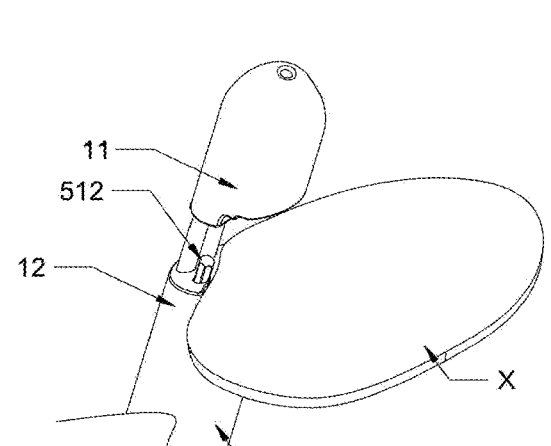
FIG. 19
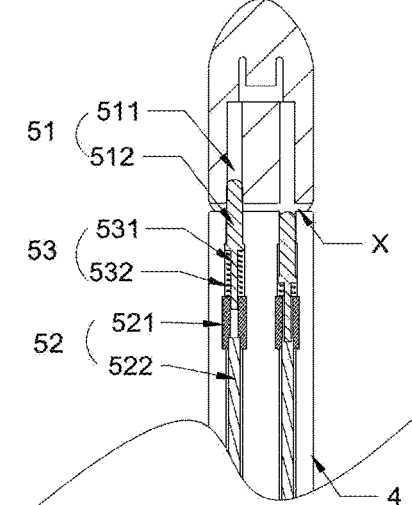
FIG. 18
FIG. 20
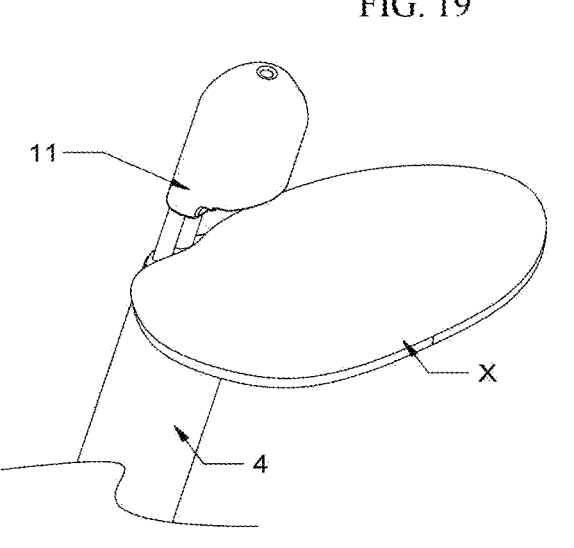
FIG. 21
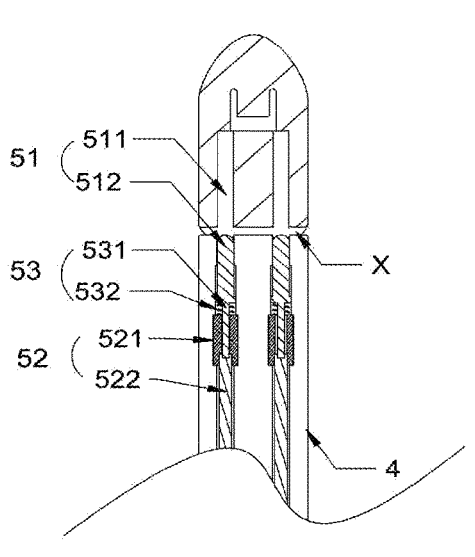
FIG. 22

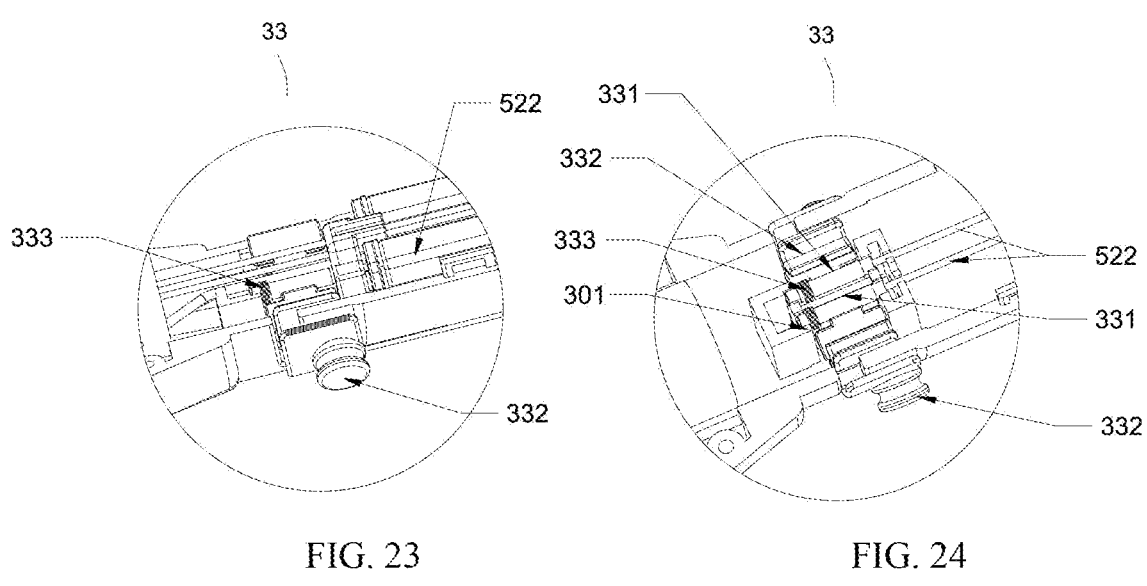
FIG. 23                    FIG. 24
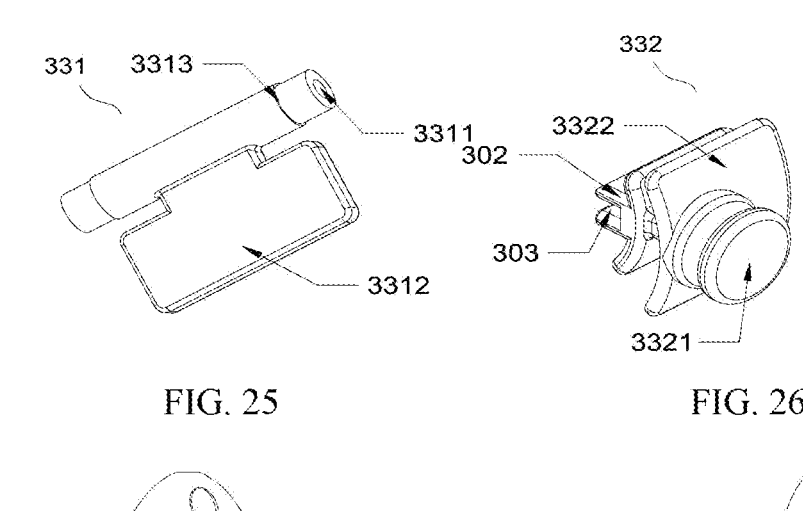
FIG. 25                    FIG. 26
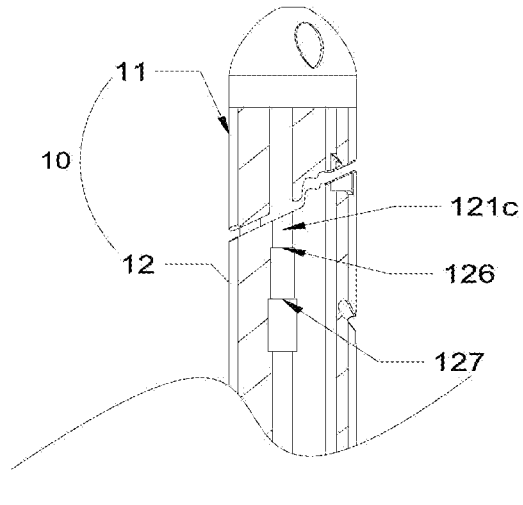
FIG. 27
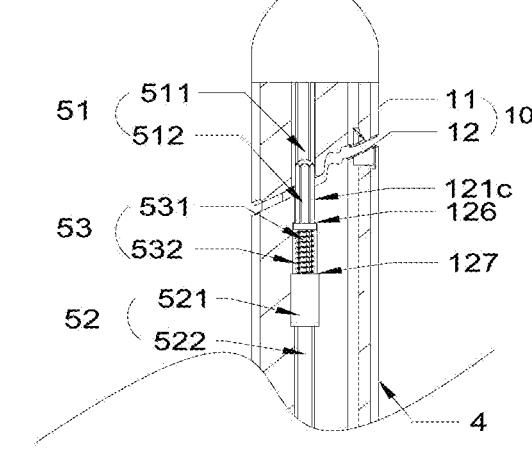
FIG. 28

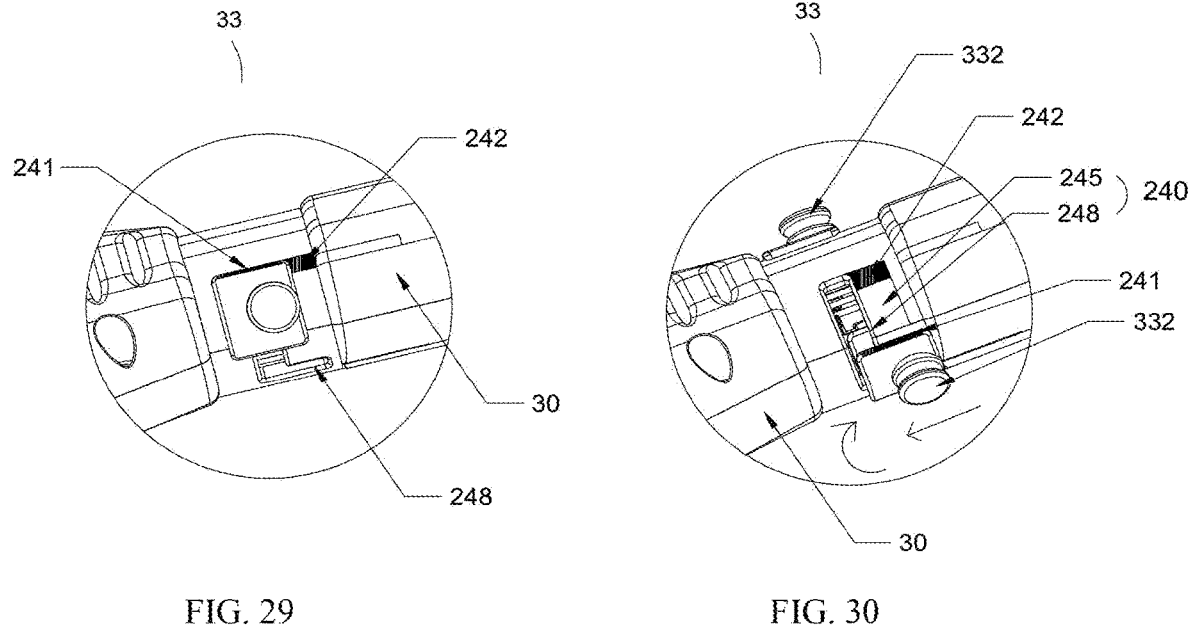
FIG. 29                    FIG. 30
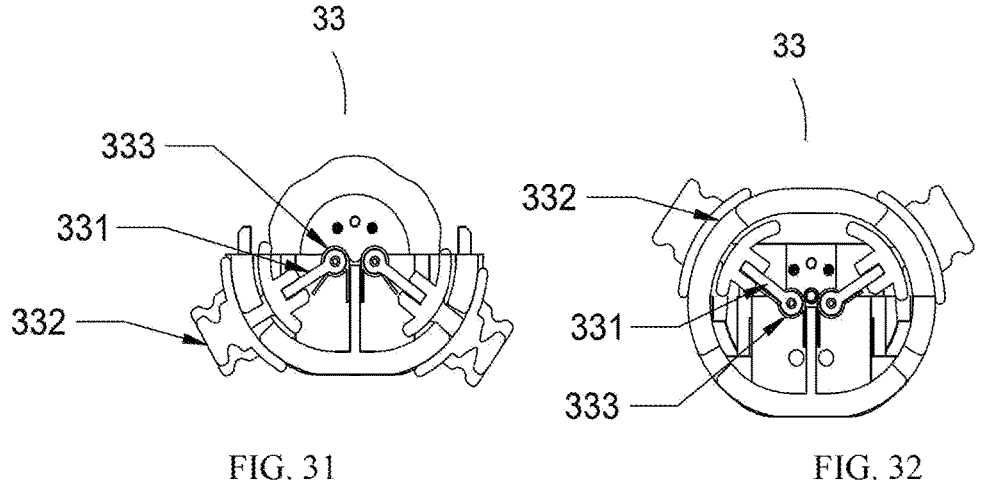
FIG. 31                    FIG. 32

VALVE REPAIR SYSTEM FOR IMPLANTING ARTIFICIAL CHORDAE TENDINEAE

The present application is a continuation of International Application No. PCT/CN2022/113960 filed on Aug. 22, 2022, which claims the priority of the Chinese patent application No. 202110976242.4, filed on Aug. 24, 2021, and entitled "valve repair system for implanting artificial chordae tendineae", which are incorporated herein by reference in their entireties.

FIELD

The subject matter relates to the field of medical devices, and more particularly, to a valve repair system for implanting artificial chordae tendineae.

BACKGROUND

Mitral valve insufficiency is one of the most common heart valve diseases. Rheumatic heart disease, mitral valve mucoid degeneration, ischemic heart disease, and cardiomyopathy are the main causes that generate lesions at valve annulus, valve leaflets, chordae tendineae, and papillary muscle of the mitral valve structure, thereby resulting in incomplete closure of the valve leaflets of the mitral valve. Surgical operation is effective for the treatment of mitral valve insufficiency, but due to the great damages to the human body, the surgical operation may cause many comorbidities and high mortality to the elderly patients and patients with many complications. Therefore, minimally invasive interventional surgery is now a better choice for most heart diseases. The main interventional treatments include artificial chordae tendineae implantation, mitral annuloplasty, and mitral valve edge-to-edge repair. The artificial chordae tendineae implanted to the valve leaflets can effectively treat the mitral valve insufficiency caused by rupture of chordae tendineae and valve leaflets prolapse, and can also maintain the physiological integrity of the mitral valve structure.

However, the existing chordae tendineae implanting and suturing devices may have problems during the puncture and suture process.

For example, an existing chordae tendineae implanting and suturing device uses a barbed needle to perform puncture and suture on the valve. The puncture point of the method is too large, resulting in great damages to the valve and a risk of valve tear. Moreover, the success rate for the needle to clasp the artificial chordae tendineae is not high, resulting in low success rate of the surgery and prolongation of the surgery period. Furthermore, only one set of artificial chordae tendineae can be implanted at a time. Thus, multiple times of suturing are required for each surgery, which are complex and time-consuming.

Another suturing device directly stitches a group of sutures on the valve leaflets that passing through the valve without winding and knotting the sutures. Such method may cause the sutures to be loose and unstable, so that satisfactory clinical effect cannot be achieved. Furthermore, only one set of artificial chordae tendineae, which is formed by sutures with a diameter in a range of 0.1 mm to 0.5 mm, can be implanted at a time. Thus, multiple operations are required for multiple sets of implantations, so that the operation is complex, time-consuming, and cannot meet the clinical needs.

At the same time, the existing implanting device also has problems during a grasping process. For example, the valve leaflets will first be grasped by a clamping device. The grasping result is judged by a grasping-verification system, so that the artificial chordae tendineae can be implanted. The principle of the grasping-verification system uses an optical fiber that produces different colors when encountering the valve leaflets and the blood, thereby determining whether the valve leaflets are grasped. However, the device structure is complex, and the optical fiber needs to enter the patient's body together with the device, which increases the surgical risk. In addition, the grasping-verification system also needs to be provided with a grasping-verification monitor, which further increases the structure complexity of the device, the process complexity, the production cost, and the surgical cost.

Another artificial chordae tendineae implanting device includes a probe device. After the device enters the heart and grasps the valve leaflets, the mechanical probe device will judge the grasping result. The mechanical device can extend the probe from the proximal clamp toward the distal clamp. The probe cannot enter the distal end when the valve leaflets are desirably grasped, thereby completing the judgement. Since whether the valve leaflets are desirably grasped is judged by the extended probe, the puncture force from the extended probe may cause damages to the valve.

SUMMARY

A valve repair system for implanting artificial chordae tendineae is provided in the present application, which includes a handle operation device at a proximal end, a valve clamping device at a distal end, at least one set of valve puncturing devices at the distal end, and a catheter connected between the handle operation device and the clamping device. The valve repair system further includes a grasping-feedback device, which is configured to determine whether a valve is correctly grasped.

The valve clamping device includes a clamping mechanism at the distal end and a clamping-control component connected to the clamping mechanism and configured to control the clamping mechanism to open or close. The clamping-control component is configured to receive the artificial chordae tendineae. The clamping mechanism includes a proximal clamp and a distal clamp.

The valve puncturing device includes a pulling loop configured to pull the artificial chordae tendineae, a connecting component configured to fix the pulling loop, and a puncture needle assembly, the pulling loop and the connecting component are received in the distal clamp.

The puncture needle assembly includes a puncture needle and a puncture hollow tube sleeved on the puncture needle, a distal end of the puncture needle assembly is received in the proximal clamp, the puncture hollow tube is detachably connected to the connecting component.

The handle operation device includes a handle, a puncturing-operation mechanism received in the handle, a clamping-operation mechanism received in the handle, and a feedback-operation mechanism received in the handle, the puncturing-operation mechanism is connected to the puncture needle assembly, the clamping-operation mechanism is connected to the clamping-control component, and the feedback-operation mechanism is connected to the grasping-feedback device.

BRIEF DESCRIPTION OF THE DRAWINGS

In order to clearly illustrate the present technology, a brief description of the drawings used in various embodiments or exemplarily implementations is given as follows. Obviously, the drawings are only some embodiments of the present disclosure. For those of ordinary skill in the art, other drawings can be obtained based on these drawings without creative work.

FIG. 5 is a diagrammatic view of a puncture needle assembly of the clamping mechanism of FIG. 2.

FIG. 6 is a diagrammatic view of a puncture hollow tube and a connecting component of the clamping mechanism of FIG. 2.

FIG. 7, FIG. 8 and FIG. 9 are diagrammatic views showing the puncture hollow tube and the connecting component of FIG. 6 assembled to each other in different embodiments.

FIG. 17 and FIG. 18 are diagrammatic views each showing multiple sets of grasping-feedback devices according to an embodiment of the present application.

FIG. 19 and FIG. 20 are diagrammatic views each showing the valve partially grasped according to an embodiment of the present application.

FIG. 21 and FIG. 22 are diagrammatic view each showing the valve completely grasped according to an embodiment of the present application.

FIG. 23 and FIG. 24 are diagrammatic views each showing a position of a knob on a handle of the valve repair system of FIG. 1.

FIG. 25 is a diagrammatic view of a connecting block on the handle of FIG. 23.

FIG. 26 is a diagrammatic view of a knob structure on the handle of FIG. 23.

FIG. 27 is a diagrammatic view of a clamping mechanism according to another embodiment of the present application.

FIG. 28 is a diagrammatic view showing a position relationship between the grasping-feedback mechanism and the clamping mechanism of FIG. 27.

FIG. 29 is a diagrammatic view showing a feedback-operation mechanism at a terminal position according to an embodiment of the present application.

FIG. 30 is a diagrammatic view showing the feedback-operation mechanism at a starting position according to an embodiment of the present application.

FIG. 31 is a cross-sectional view of the feedback-operation mechanism at the starting position of FIG. 30.

FIG. 32 is a cross-sectional view showing the feedback-operation mechanism at the terminal position of FIG. 29.

DETAILED DESCRIPTION

Figure 1:
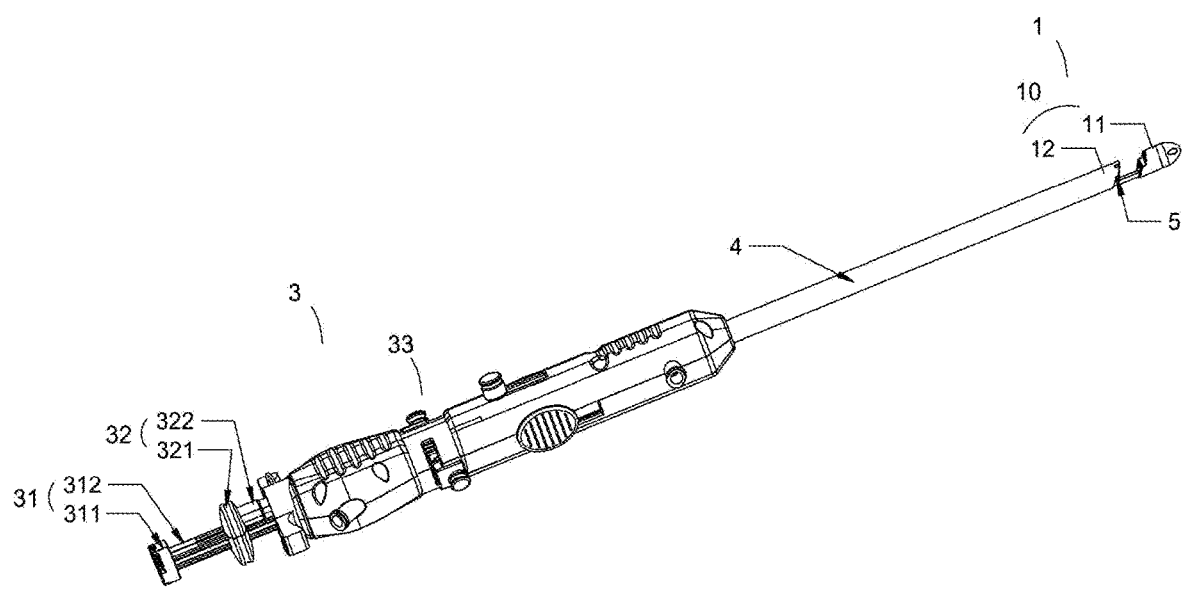
FIG. 1 is a diagrammatic view of a valve repair system for implanting artificial chordae tendineae according to an embodiment of the present application.

Implementations of the present disclosure will now be described, by way of embodiments only, with reference to the drawings to make the purpose, technical solutions, and advantages of the present application clear. It should be understood that the embodiments are illustrative only but not considered as limiting the present disclosure.

It should be noted that when a component is referred to as being or "fixed on" or "arranged on" another component, the component can be directly or indirectly on another component. When a component is considered to be "connected to" another component, the component can be directly or indirectly connected to another component.

Orientations or positional relationships indicated by terms "on", "under", "left", "right", "front", "back", "vertical", "horizontal", "top", "bottom", "inside", and "outside" are relative to the orientations or positional relationships shown in the attached drawings.

The terms "axial" refers to a length direction of the entire device or component, and the term "radial" refers to a direction perpendicular to the axial direction.

The term "circumference" refers to a periphery direction.

The terms "first" and "second" are only used for describing purpose, and not intended to indicate or imply the relative importance or to imply the quantity of the features referred to. The term "multiple" means two or more unless otherwise specified.

The term "distal end" and "proximal end" are described based on an operator. A position close to the operator is considered as proximal, and a position away from the operator is considered as distal.

The above terms are illustrative only but not considered as limiting the present disclosure.

Implementations of the disclosure will now be described, by way of embodiments only, with reference to the drawings.

Referring to FIGS. 1 to 32, a valve repair system for implanting artificial chordae tendineae is provided according to the present application, which includes a handle operation device 3 at a proximal end, a valve clamping device 1 at a distal end, at least one set of valve puncturing device 2 at the distal end, a catheter 4 arranged between the valve clamping device 1 and the handle operation device 3, and a grasping-feedback device 5 for determining whether the valve has been correctly grasped. The valve clamping device 1 includes a clamping mechanism 10 at the distal end and a clamping-control component 13. The clamping-control component 13 is connected to the clamping mechanism 10 for controlling the clamping mechanism 10 to open or close. The clamping mechanism 10 includes a proximal clamp 12 and a distal clamp 11.

The valve puncturing device 2 includes a pulling loop 21 for pulling the artificial chordae tendineae M, a connecting component 22 for fixing the pulling loop 21, and a puncture needle assembly 23. The puncture needle assembly 23 includes a puncture needle 231 and a puncture hollow tube 232 sleeved on the puncture needle 231. The puncture hollow tube 232 is detachably connected to the connecting component 22. The puncture hollow tube 232 can move together with the puncture needle 231. The pulling loop 21 and the connecting component 22 are received in the distal clamp 11. The distal end of the puncture needle assembly 23 is received in the proximal clamp 12. The artificial chordae tendineae M extends through the clamping-control component 13.

The handle operation device 3 includes a handle 30, a puncturing-operation mechanism 31 arranged in the handle 30, a clamping-operation mechanism 32, and a feedback-operation mechanism 33. The puncturing-operation mechanism 31 is connected to the puncture needle assembly 23. The clamping-operation mechanism 32 is connected to the clamping-control component 13. The feedback-operation mechanism 33 is connected to a feedback-control mechanism 52 of the grasping-feedback device 5.

The valve repair system for implanting artificial chordae tendineae mainly includes four portions, that is, the valve clamping device 1, the valve puncturing device 2, the grasping-feedback device 5, and the handle operation device 3. The catheter 4 is connected between the valve clamping device 1 and the handle operation device 3.

Figures 2, 3, 4:
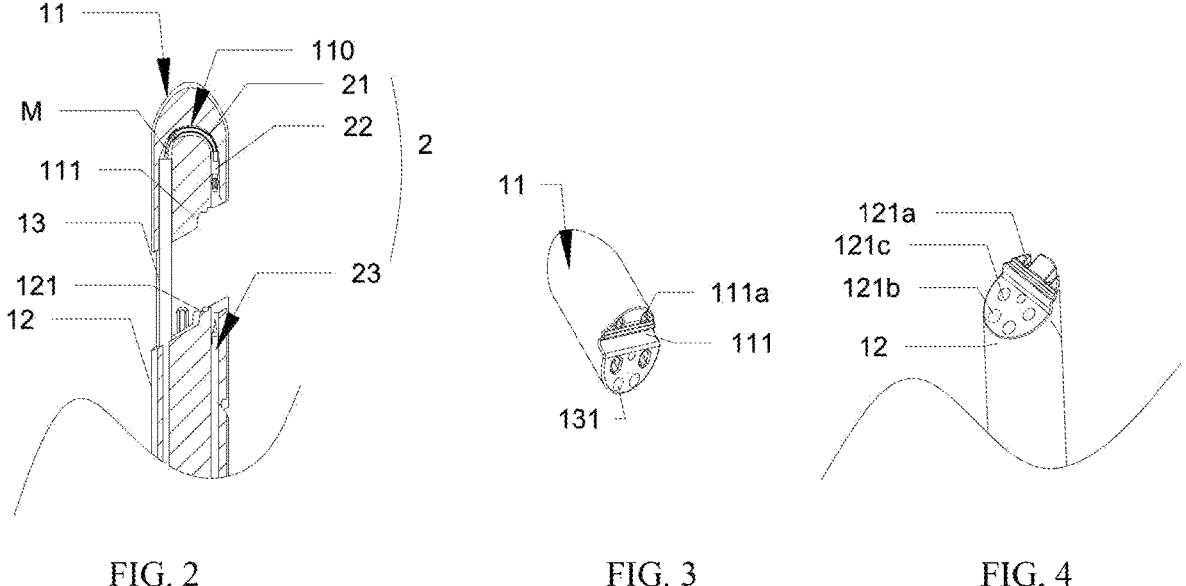
FIG. 2 is a cross-sectional view of a clamping mechanism of the valve repair system of FIG. 1.
FIG. 3 is a diagrammatic view of a distal clamp of the clamping mechanism of FIG. 2.
FIG. 4 is a diagrammatic view of a proximal clamp of the clamping mechanism of FIG. 2.

Referring FIGS. 2 to 4, the clamping mechanism 10 of the valve clamping device 1 is used to grasp the valve. After the valve is grasp, the valve is punctured by the valve puncturing device 2. The artificial chordae tendineae M extends through the valve and is then pulled out of the body to be knotted, and is then sent back to the suturing position on the valve. The clamping mechanism 10 includes the distal clamp 11 at the distal end and the proximal clamp 12 opposite to the distal clamp 11. Each of the distal clamp 11 and the proximal clamp 12 has a clamping surface for grasping the valve. The distal clamp 11 has a conical shape. The proximal clamp 12 is fixed to or integrally formed with the catheter 4.

The clamping surface 111 of the distal clamp 11 and the clamping surface 121 of the proximal clamp 12 are both inclined surfaces, and the inclination degree may be 60 degrees. To firmly grasp the valve, the clamping surfaces 111 and 121 are both zigzag-shaped to increase the grasping force. The clamping mechanism 10 may be made of a polymer material such as ABS, PC, and PEEK, or a metal material such as stainless steel and cobalt chromium alloy.

The distal clamp 11 is fixed to the clamping-control component 13. The clamping-control component 13 sequentially extends through the proximal clamp 12 and the catheter 4. The distal end of the clamping-control component 13 is fixed to the distal clamp 11, and the proximal end of the clamping-control component 13 protrudes from the catheter 4 and is connected to the clamping-operation mechanism 32. Under the function of the clamping-operation mechanism 32, the distal clamp 11 and the proximal clamp 12 can move toward each other for grasping or separate from each other. The clamping-control component 13 is rod-shaped, which may be a solid rod or a hollow rod. In order to fully utilize various components, the clamping-control component 13 is a hollow rod, and the sutures form the artificial chordae tendineae M. The number of clamping-control component(s) 13 may be at least one or multiple according to the number of the artificial chordae tendineae M. The clamping-control component 13 and the distal clamp 11 may be connected to each other such as by welding, clamping, or gluing.

Referring to FIGS. 2 to 4, the distal clamp 11 defines a receiving chamber 110 for receiving both of the pulling loop 21 and the connecting component 22. One end of the receiving chamber 110 is connected to the clamping-control component 13, and another end of the receiving chamber 110 extends to the clamping surface 111 of the distal clamp 11. Since the pulling loop 21 will pull the artificial chordae tendineae M to extend the connecting component 22 to connect the puncture needle assembly 23, an opening 111a of the receiving chamber 110 on the clamping surface 111 of the distal clamp 11 corresponds to the position of the puncture needle assembly 23. That is, the receiving chamber 110 is U-shape, with an end communicating with an inner chamber 131 for receiving the clamping-control component 13. A U-shaped closed end of the artificial chordae tendineae M is pulled from the clamping-control component 13 to the receiving chamber 110. The position of connecting component 22 in the receiving chamber 110 corresponds to the position of the opening 111a defined on the clamping surface 111 of the distal clamp 11. The proximal clamp 12 defines a puncture hole 121a allowing the puncture needle assembly 23 to extend through, a clamping hole 121b allowing the clamping-control component 13 to extend through, and a through hole 121c allowing a main feedback component 51 to extend through.

The artificial chordae tendineae M may typically use e-PTFE sutures or PET sutures, which has an outer diameter in a range of 0.2 mm to 0.5 mm.

The distal clamp 11 further defines the inner chamber 131 for receiving the clamping-control component 13. The inner chamber 131 is connected to the receiving chamber 110.

Referring to FIG. 6, the connecting component 22 is used to connect the puncture needle assembly 23 to the pulling loop 21. The connecting component 22 has a prism structure, for example, the connecting component 22 has a cylindrical structure without edges and corners, such as a cylinder, an elliptical cylinder, or a prism with smoothly transitional corners. In this embodiment, the connecting component 22 is a cylinder. One end of the connecting component 22 is fixed to the pulling loop 21, and another end of the connecting component 22 is detachably connected to puncture needle assembly 23. The connecting component 22 may be made of a metal material such as stainless steel and cobalt chromium alloy, or made of a polymer material.

The pulling loop 21 is annular. The U-shaped closed end of the artificial chordae tendineae M passes through the pulling loop 21. The pulling loop 21 is connected to the connecting component 22 such as by crimping, welding, or gluing. The pulling loop 21 may be a single strand or multiple strands made of metal or polymer.

Referring to FIG. 5, in the valve puncturing device 2, the puncture needle 231 and the puncture hollow tube 232 may be in clearance fit or sliding fit. The proximal end of the puncture needle 231 is connected to the puncturing-operation mechanism 31 of the handle operation device 3. The puncture needle 231 further extends through the catheter 4 to the clamping surface 121 of the proximal clamp 12. In one embodiment, the proximal clamp 12 extends to the puncture hole 121a on the clamping surface 121. The distal end of the puncture needle 231 is close to the clamping surface 121 of the proximal clamp 12.

The puncture hollow tube 232 is a component for connecting the connecting component 22. The puncture hollow tube 232 is a hollow tube with a limited inner diameter. The puncture needle 231 can be operated to puncture the valve at a time, which also drives the puncture hollow tube 232 to move. Then, the puncture hollow tube 232 is detachably connected to the connecting component 22. The distal end of the puncture hollow tube 232 is provided with a limiting head 2321 for limiting a length of the puncture needle 231 from the puncture hollow tube 232. The taper of the tip at the distal end of the puncture needle 231 is equal to the taper of the outer wall of the limiting head 2321 at the distal end of the puncture hollow tube 232, which can increase the effectiveness of puncture and reduce the puncture damages.

The connecting component 22 and the puncture hollow tube 232 are detachably connected to each other such as by screw connection, snap fit, insertion connection, or interference fit.

Referring to FIG. 7, the screw connection is realized by defining external threads at the connecting component 22 and internal threads at the distal end of the puncture hollow tube 232, so that the connecting component 22 can be inserted into and screwed to the puncture hollow tube 232.

Referring to FIGS. 6 and 8, the snap fit is realized by arranging a latch 221 at the proximal end of the connecting component 22 and a slot 2322 at the distal end of the puncture hollow tube 232, so that the latch 221 is inserted into the slot 2322 to connect the connecting component 22 and the puncture hollow tube 232 together. The latch 221 includes a fitting portion 2211, a groove 2212, and a chamfer 2213. The fitting portion 2211 is a structure for connecting the puncture hollow tube 232 by snap fit. The groove 2212 provides deformation space for the snap fit. The chamfer 2213 improves the smoothness of the puncture hollow tube 232 when inserting into the slot 2322. The distal end of the connecting component 22 is provided with a radial limiting portion 222. The radial limiting portion 222 is engaged with the receiving chamber 131 of the distal clamp 11 to prevent the radial position of the connecting component 22 from being changed in the distal clamp 11.

Referring to FIG. 9, the insertion connection is realized by defining at least one circle of oblique slots or teeth 223 at the outer wall of the proximal end of the connecting component 22, and correspondingly defining at least one circle of teeth or oblique slots 2323 at the inner wall of the puncture hollow tube 2325, so that the teeth 223 are engaged in the oblique slots 2323 to connect the connecting component 22 to the puncture hollow tube 232.

In order to implant multiple sets of sutures at once to form the artificial chordae tendineae M, multiple sets of clamping-control components 13, multiple sets of valve puncturing devices 2, and multiple sets of grasping-feedback devices 5 are provided. For example, a pair of clamping-control components 13 spaced from each other, a pair of valve puncturing devices 2 spaced from each other, and a pair of grasping-feedback devices 5 spaced from each other are provided. That is, multiple sets of (such as a pair of) clamping-control component 13, multiple sets of (such as a pair of) receiving chambers 110, multiple sets of (such as a pair of) puncture needle assemblies 23, and multiple sets of (such as a pair of) grasping-feedback devices 5 are provided.

Referring to FIGS. 10 to 13, the grasping-feedback device 5 includes a grasping-feedback mechanism 51 and a feedback-control mechanism 52 connected to the grasping-feedback mechanism 51. The grasping-feedback mechanism 51 includes a main feedback component 512 arranged in the proximal clamp 12 and an auxiliary feedback component 511 arranged in the distal clamp 11. The main feedback component 512 is opposite to the auxiliary feedback component 511. The feedback-control mechanism 52 includes a feedback-control component 522 inserted into the catheter 4. The proximal end of the feedback-control component 522 extends to the proximal end of the catheter 4 and is connected to the feedback-operation mechanism 33. The distal end of the feedback-control component 522 is elastically connected to the main feedback component 512 for driving the main feedback component 512 to rotate. The main feedback component 512 and the auxiliary feedback component 511 are in insertion connection, thereby limiting the rotation of the main feedback component 512 and the feedback-control component 522.

Referring to FIGS. 10 to 13, the grasping-feedback device 5 includes two main portions, that is, the grasping-feedback mechanism 51 and the feedback-control mechanism 52.

Figures 10, 11, 12, 13, 14, 15, 16:
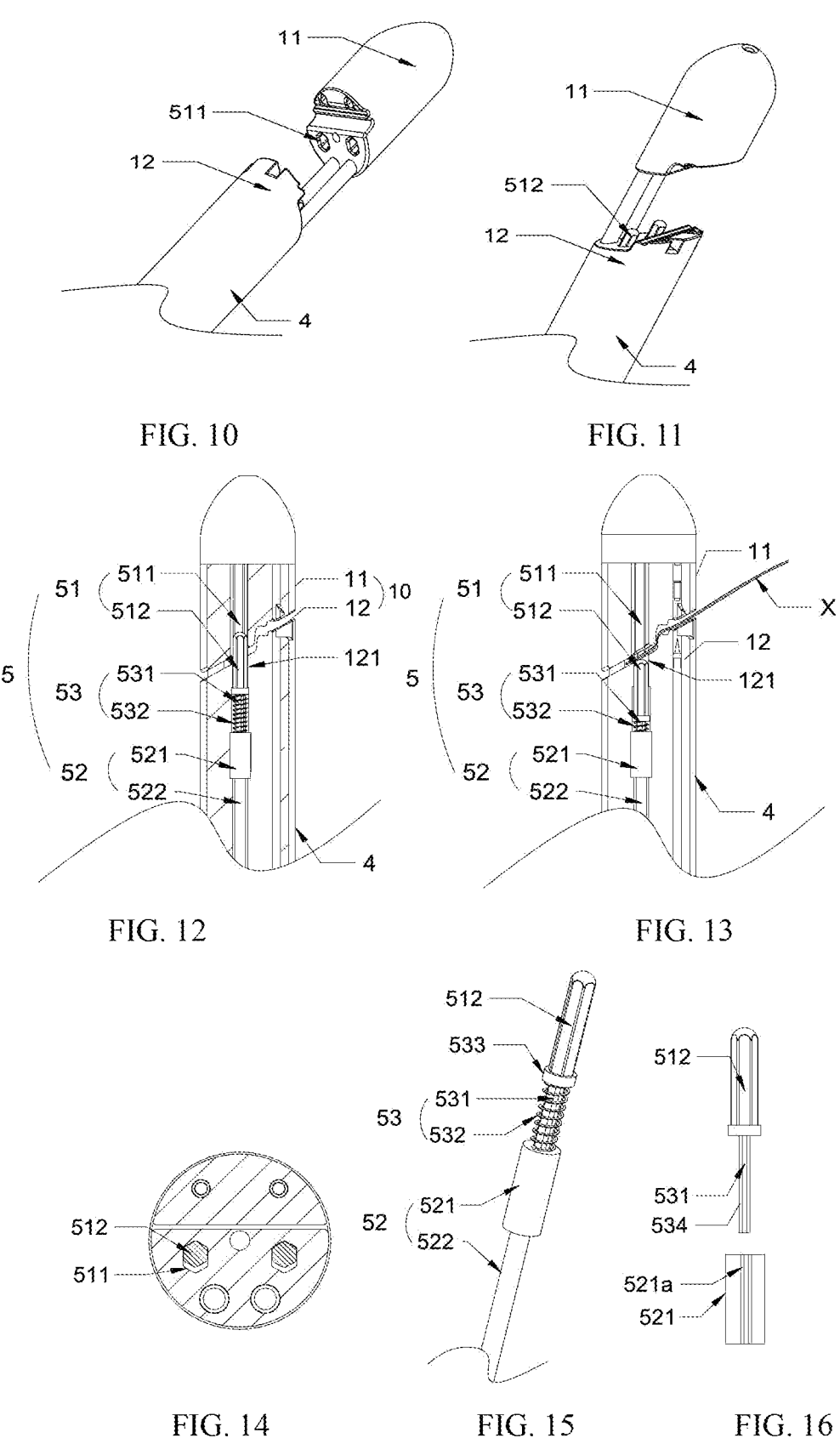
FIG. 10 and FIG. 11 are diagrammatic views each showing a position of a grasping-feedback device in the clamping mechanism of FIG. 2.
FIG. 12 and FIG. 13 are cross-sectional views each showing the position of the grasping-feedback device in the clamping mechanism of FIG. 2.
FIG. 14 is a sectional view showing a main feedback component inserted into an auxiliary feedback component of the grasping-feedback device of FIG. 12.
FIG. 15 is a diagrammatic view showing a positional relationship among a connecting assembly, a feedback-control component, and the main feedback component of the grasping-feedback device of FIG. 12.
FIG. 16 is a diagrammatic view showing a connecting component and a radial limiting component of FIG. 15.

The grasping-feedback device 5 of the present application is installed in the valve repair system to determine whether the clamping mechanism 10 of the valve repair system has successfully clamped the valve. The grasping-feedback mechanism 51 includes the main feedback component 512 and the auxiliary feedback component 511. The main feedback component 512 and the auxiliary feedback component 511 are respectively arranged on the proximal clamp 12 and the distal clamp 11 of the clamping mechanism 10. When the proximal clamp 12 and the distal clamp 11 cooperatively grasp the valve, the main feedback component 512 and the auxiliary feedback component 511 are arranged on two sides of the valve. To obtain feedback about whether the valve has been grasped can be achieved, it is necessary to determine whether the main feedback component 512 and the auxiliary feedback component 511 are in insertion. Referring to FIG. 13, when the valve has been fully grasped, the main feedback component 512 and the auxiliary feedback component 511 are blocked by the valve X and cannot be in insertion connection. The feedback-operation mechanism 33 in the handle 30 drives the main feedback component 512 to rotate through the feedback-control component 522 in the catheter 4, indicating that the valve has been grasped. Referring to FIG. 12, when the valve is not grasped or is incomplete clamped, the main feedback component 512 and the auxiliary feedback component 511 are in insertion connection. The radial position of the main feedback component 512 is limited by the auxiliary feedback component 511, so that the main feedback component 512 cannot rotate. Therefore, even when the main feedback component 512 is connected to feedback-control component 522, the feedback-control component 522 cannot rotate. Thus, a failure of the grasping is indicated when the operator cannot rotate the feedback-control component 522. Therefore, the grasping result can be obtained by determining whether the feedback-control component 522 can rotate.

In at least one embodiment, one of the main feedback component 512 and the auxiliary feedback component 511 is a feedback plug, and another of the main feedback component 512 and the auxiliary feedback component 511 is a feedback socket matching the feedback plug. The feedback plug and the feedback socket are in key connection, spline connection, or profile connection with the feedback socket to realize the radial limitation. A limiting position may also be provided inside the feedback socket, so that after the feedback plug is inserted into the feedback socket, the limiting position can prevent the feedback plug and the feedback socket from rotating relative to each other. That is, after the feedback plug is inserted into the feedback socket, the main feedback component 512 is prevented from rotating. The insertion connection of the main feedback component 512 and the auxiliary feedback component 511 may be realized by two ways. The first way is to arrange the main feedback component 512 as a feedback plug on and the auxiliary feedback component 511 as a feedback socket. The second way is to arrange the auxiliary feedback component 511 as a feedback plug on and the main feedback component 512 as a feedback socket. Both ways are implementable. For example, in a first embodiment as shown in FIGS. 2 to 4 and 14, the auxiliary feedback component 511 is a feedback socket defined on the clamping surface 111 of the distal clamp 11, and the main feedback component 512 is a feedback plug that extends from the inside of the proximal clamp 12 to the clamping surface 121. The through hole 121c is defined on the proximal clamp 12. The feedback plug as the main feedback component 512 can extend through the through hole 121c. The feedback socket as the auxiliary feedback component 511 is defined on the corresponding distal clamp 11. The feedback plug needs to resist against the valve X. The head of the feedback plug may be smooth without any edge and corner. Since the auxiliary feedback component 511 and the main feedback component 512 can be in insertion connection, the auxiliary feedback component 511 and the main feedback component 512 can axially move relative to each other to realize or remove the insertion connection. However, after the insertion connection, the auxiliary feedback component 511 and the main feedback component 512 cannot rotate radially (or circumferentially) with each other.

Referring to FIGS. 27 and 28, the proximal clamp 12 defines the through hole 121c allowing the main feedback component 512 to extend through. A limiting component is arranged in the through hole 121c to prevent the main feedback component 512 from separating from the proximal clamp 12. In one embodiment, the limiting component includes a step 126 and a step 127 on the inner wall of the through hole 121c. That is, the through hole 121c is a stepped hole. The feedback-connecting assembly 531 of the main feedback component 512 is limited below the step 126, and a radial limiting component 521 is limited below the step 127. In addition to the steps 126 and 127, the limiting component may also be a protrusion or a convex ring on the inner wall of the through hole 121c.

The insertion connection between the main feedback component 512 and the auxiliary feedback component 511 may be realized by three embodiments.

The first embodiment is a loose key connection. The feedback plug and the feedback socket are in key connection or spline connection. The key connection is a flat key connection. A flat key is arranged on the feedback plug, and a flat key slot is defined in the feedback socket as the limiting position. When the feedback plug is inserted into the feedback socket, the flat key is inserted into the flat key slot, so that the feedback plug cannot rotate in the feedback socket. The same structure may also be applied to the spline connection, which will not be repeated.

The second embodiment is a profile connection. The profile connection is a detachable connection that engages a prism body having a non-circular cross-section with a hole having the same contour, thereby transmitting motion and torque. That is, the feedback plug is a prism body having a non-circular cross-section. The feedback socket is a hole with the same contour, and the inner wall of the feedback socket is provided with the limiting position. Since each of the feedback plug and the feedback socket has a non-circular cross-section and the gap therebetween inhibits the rotation of the feedback plug in the feedback socket, a radial limitation can be achieved between the feedback plug and the feedback socket. The profile connection is a profile connection using polygonal cross-sections, for example, triangle, rectangular, pentagonal, or hexagonal cross-sections. The profile connection may also be a profile connection using non-circular cross-sections. All structures having non-circular surfaces are applicable to the present application. Referring to FIG. 14, in one embodiment, hexagonal cross-sections are used in the profile connection. That is, each of the main feedback component 512 and the auxiliary feedback component 511 has a hexagonal cross-section, and the main feedback component 512 and the auxiliary feedback component 511 are in clearance fit.

The above two embodiments are that the feedback plug and the feedback socket have the same shape, and the gap therebetween inhibits the rotation of the feedback plug.

The third embodiment is a resisting connection, which is different from the above two embodiments in that the shape of the feedback plug is different from the shape of the feedback socket. A limiting position is provided in the feedback socket, which can prevent the feedback plug from rotating after the feedback plug is inserted into the feedback socket. When the feedback plug is inserted into the feedback socket, the feedback plug is resisted against the limiting position, thereby limiting the position of the main feedback component 512 so that the main feedback component 512 cannot rotate. In this embodiment, the limiting position is provided on the inner wall of the feedback socket, and the number of the limiting position(s) may be one or multiple. The limiting position may be a groove or a convex platform axially arranged. The feedback plug is resisted against the groove or the convex platform of the limiting position to prevent the feedback plug to rotate relative to the feedback socket.

Referring to FIGS. 12, 13, 15, and 16, the proximal end of the main feedback component 512 is connected to a connecting assembly 53. The connecting assembly 53 is used to connect the main feedback component 512 to the feedback-control component 522. The connecting assembly 53 is elastically connected to the feedback-control component 522. The distal end of the feedback-control component 522 is provided with the radial limiting component 521. The connecting assembly 53 is elastically connected to the radial limiting component 521 of the feedback-control component 522, so that the connecting assembly 53 can drive the main feedback component 512 to radially rotate. The connecting assembly 53 includes a feedback-connecting component 531 at the proximal end of the main feedback component 512 and an elastic component 532 for returning the main feedback component 512 to its original position after the main feedback component 512 is pressed. The elastic component 532 can be sleeved on the feedback-connecting component 531 or the radial limiting component 521. The elastic component 532 allows the main feedback component 512 to axially move. When the main feedback component 512 encounters the valve X, the main feedback component 512 is elastically resisted against the valve X without any damage to the valve X. Under such state, the elastic component 532 is compressed, and the proximal end of the main feedback component 512 moves back towards the feedback-control component 522. Without the valve X, the main feedback component 512 can be inserted into the auxiliary feedback component 511 under the function of the elastic component 532.

The elastic component 532 may be a spring or an elastic sleeve. The elastic component 532 is sleeved on the feedback-connecting component 531 or the radial limiting component 521. A stopper 533, such as a stopping ring or a stopping block, is arranged on the feedback-connecting component 531 or the radial limiting component 521, which can prevent the elastic component 532 from separating from the feedback-connecting component 531 or the radial limiting component 521. Referring to FIG. 15, the elastic component 532 is sleeved on the feedback-connecting component 531. The stopper 533 is arranged at the distal end of the feedback-connecting component 531. Two ends of the elastic component 532 are respectively resisted against the stopper 533 and the distal end of the radial limiting component 521. The feedback-connecting component 531 is inserted into the radial limiting component 521.

In other embodiments, the elastic component 532 may also be sleeved on the radial limiting component 521. The stopper 533 may be arranged on the radial limiting component 521. The two ends of the elastic component 532 may be respectively resisted against the stopper 533 and the proximal end of the feedback-connecting component 531. The radial limiting component 521 is inserted into the feedback-connecting component 531.

The feedback-connecting component 531 and the radial limiting component 521 of the feedback-control component 522 are in insertion connection, which allows the feedback-connecting component 531 to axially move relative to the radial limiting component 521, and also allows the feedback-connecting component 531 to radially rotate together with the radial limiting component 521. The feedback-connecting component 531 may be inserted into the radial limiting component 521, and the radial limiting component 521 may also be inserted into the feedback-connecting component 531. The insertion connection between the feedback-connecting component 531 and the radial limiting component 521 may be realized by various embodiments, which are similar to the insertion connection between the feedback plug and the feedback socket.

The first embodiment is a loose key connection such as key connection or spline connection, which can refer to the description about the loose key connection between the feedback plug and the feedback socket and will not be repeated.

The second embodiment is a profile connection, which can refer to the description about the profile connection between the feedback plug and the feedback socket and will not be repeated. Referring to FIG. 16, in this embodiment, the feedback-connecting component 531 has a strip or cylindrical structure, and two guiding columns 534 are arranged on two sides of the cylindrical structure. A strip-shaped or cylindrical-shaped inner cavity 521a with two guiding grooves is defined in the radial limiting component 521 in the axial direction. The shape of the inner cavity 521 is the same as that of the feedback-connecting component 531. The feedback-connecting component 531 and the inner cavity 52 may be in sliding fit or clearance fit, but the gap inhibits the rotation of the feedback-connecting component 531.

The third embodiment is a resisting connection. One of the feedback-connecting component 531 and the radial limiting component 521 defines a limiting groove, and another of the feedback-connecting component 531 and the radial limiting component 521 is provided with a limiting component. Both the limiting groove and the limiting component extend in the axial direction. After the radial limiting component 521 is inserted into the feedback-connecting component 531, the feedback-connecting component 531 can axially move relative to the radial limiting component 521, and also can radially rotate together with the radial limiting component 521. The limiting component is resisted in the limiting groove to inhibit the rotation. The shapes of the limiting groove and the limiting component may be different from each other, only requiring that the limiting component can be resisted in the limiting groove. For example, the limiting groove is a circle of grooves, and limiting component is a limiting tooth. The radial rotation is prevented when the limiting tooth is resisted in any one of the grooves.

The insertion length between the radial limiting component 521 and the feedback-connecting component 531 meets the following requirement:

When the elastic component 532 is in a free state, the radial limiting component 521 and the feedback-connecting component 531 are still in insertion connection. That is, a connection relationship remains between the radial limiting component 521 and the feedback-connecting component 531 without separation.

Referring to FIGS. 17 to 22, when the valve clamping device 1 grasps the valve X, two situations may exist, including that the valve X may be completely grasped or incompletely grasped. The completely grasping situation means that the valve X is successfully and desirably grasped. The incompletely grasping situation means that only one side of the valve X is grasped but the other side of the valve X is not grasped, so that the artificial chordae tendineae M cannot be implanted. Therefore, two or more sets of grasping-feedback mechanisms 51 are required, and adjacent sets of grasping-feedback mechanisms 51 are spaced from each other. Each grasping-feedback mechanism 51 is connected to one feedback-control mechanism 52. FIGS. 19 and 20 show an incompletely grasping situation. The main feedback component 512 and the auxiliary feedback component 511 of one set of grasping-feedback mechanism 51 are in insertion connection, so the corresponding feedback-control component 522 cannot rotate. Another feedback-control component 522 can rotate, indicating that the valve X is grasped at the corresponding position. FIGS. 21 and 22 show a completely grasping situation. The main feedback components 512 of the two sets of grasping-feedback mechanisms 51 are blocked by the valve X and cannot be inserted into the auxiliary feedback components 511. Thus, the feedback-control components 522 can both rotate.

The catheter 4 defines multiple cavities that extend through the proximal and distal ends. The cavities include at least one set of first cavities allowing the clamping-control component 13 to extend through, at least one set of second cavities allowing the puncture needle assembly 23 to extend through, and at least one set of third cavities allowing the feedback-control component 522 to extend through.

Referring to FIGS. 1 to 9, the handle operation device 3 includes the handle 30, the puncturing-operation mechanism 31 received in the handle 30, the clamping-operation mechanism 32, and the feedback-operation mechanism 33.

The puncturing-operation mechanism 31 includes two puncture operation rods 312, which are connected to the proximal end of the puncture needle 231 and the proximal end of the puncture hollow tube 232, respectively. The proximal end of the puncture operation rod 312 protrudes from the proximal end of the handle 30 and connects to the puncture handle 311 for easy operation.

The clamping-operation mechanism 32 includes a clamping operation rod 322 connected to the proximal end of the clamping-control component 13. The proximal end of the clamping operation rod 322 protrudes from the proximal end of the handle 30 and connects to the clamping handle 321 for easy operation.

Referring to FIGS. 23 to 26, the feedback-operation mechanism 33 includes a connecting block 331 connected to the proximal end of the feedback-control component 522 and a knob 332 slidably connected to the handle 30 in the axial direction. The knob 332 is further connected to the connecting block 331 to drive the connecting block 331 to rotate. A torsion spring 333 is sleeved on the connecting block 331, which can return the connecting block 331 to its original position.

In one embodiment, the connecting block 331 includes a shaft 3311 and a blade 3312 extending from one side of the shaft 3311. The torsion spring 333 is sleeved on the shaft 3311. A protrusion or a stopping ring 3313 is provided on each end of the shaft 3311, which can limit the position of the torsion spring 333. One end of the torsion spring 333 is fixed to or resisted against a rib 301 inside the handle 30, and another end of the torsion spring 333 is resisted against or fixed to the blade 3312. The shaft 3311 is fixed to the proximal end of the feedback-control component 522 such as by welding, gluing, or snap fit. The knob 332 includes a knob body 3321. A curve plate 3322 and a fitting component 302 are sequentially arranged behind the knob body 3321. A sliding groove 303 is defined on the fitting component 302, which extends through two ends of the fitting component 302. The blade 3312 of the connecting block 331 is inserted into the sliding groove 303, and the blade 3312 can axially slide in the sliding groove 303.

The knob 332 can slide circumferentially around the handle 30. That is, the knob 332 can rotate around the shaft 3311 to drive the connecting block 331 to rotate. Thus, the feedback-control component 522 is driven to rotate. At the same time, the torsion spring 333 stores torque or rotation energy to return the connecting block 331 to its original position.

Referring to FIGS. 29 and 30, a sliding component 240 is further provided on the handle 30. The sliding component 240 defines a limiting groove 248 for limiting the position of the knob 332 along its rotating direction. The limiting groove 248 is L-shaped, which includes a stopping portion extending in the axial direction of the handle 30 and a sliding portion extending perpendicular to the axial direction. The sliding component 240 further includes a curve sliding surface 245. A central axis of the curve sliding surface 245 is aligned with the shaft 3311 of the connecting block 331. The knob 332 can slide on the sliding component 240, and further extends through the limiting groove 248 to connect to the connecting block 331. The knob 332 can move in the circumferential direction of the sliding component 240, thereby driving the connecting block 331 to rotate. The curve plate 3322 behind the knob body 3321 matches the curve sliding surface 245 in shape. The curve plate 3322 can slide relative to the curve sliding surface 245, and the curve sliding surface 245 can limit the position of the knob 332.

The handle 30 and the knob 332 are provided with a marking 242 and a mark 241, respectively. When the knob 332 is rotated to cause the two markings 241 and 242 to overlap with each other, the valve clamping device 1 has successfully grasped the valve. If the knob 332 cannot be rotated or the two markings 241 and 242 cannot overlap with each other, the valve clamping device 1 fails to grasp the valve.

The implementation process is as follows. The starting position is shown in FIGS. 29 to 32. The connecting block 331 rotates around a central axis of the torsion spring 260. The torsion spring 333 stores a torque or rotation energy for pulling the connecting block 331 back to the starting position. The blade 3312 of the connecting block 331 is inserted into the sliding groove 303 of the knob 332, and can axially slide in the sliding groove 30. The curve plate 3322 of the knob 332 matches the curve sliding surface 245 of the handle 30, and the position of the knob 332 along the radial direction is limited. The knob 332 can rotate around the shaft 3311, and the shaft 3311 rotates together with the rotating connecting block 331. The knob 332 can also slide on the connecting block 331 along the axial direction of the shaft 3311. When the knob 332 or the connecting block 331 is rotated to the starting position, the knob 332 can move axially into the stopping portion of the limiting groove 248 of the handle 30, thereby overcoming the torque or rotation energy of the torsion spring 333. When the feedback of the grasping result is required, the knob 332 slides out of the stopping portion of the limiting groove 248 and into the sliding portion of the limiting groove 248. At this time, the torque or rotation energy of the torsion spring 333 attempts to pull the knob 332 back to the starting position. If the valve is successfully grasped, the knob 332 is rotated to the terminal position shown in FIG. 29. That is, the marks 241 and 242 overlap with each other. Otherwise, the knob 332 cannot be rotated to the terminal position, and the marks 241 and 242 will not overlap with each other.

The present application includes a connecting component and a puncture needle assembly cooperating with the connecting component. The connecting component is connected to the puncture hollow tube. The puncture needle can drive the puncture hollow tube to move together with the puncture needle. The connection between the puncture hollow tube and the connecting component can be realized by operating the puncture needle. Since the connecting component and the puncture hollow tube are connected to form a longitudinal structure, puncturing damages can be reduced, and the withdrawn of the puncture hollow tube can be smooth. A set of pulling loops can pull the U-shaped closed ends of a set of artificial chordae tendineae. The puncture needle assembly passes through the valve and cooperates with the connecting component. Thus, the U-shaped closed end and the open end can be pulled out of the human body, and then twisted and knotted outside the human body and sent back into the heart. The annular structure of the pulling loop can not only pull the conventional suture with a diameter in a range of 0.1 mm to 0.5 mm, but also the suture with a diameter greater than or equal to 0.5 mm, making it suitable for sutures with various diameters. Multiple sets of valve puncturing devices can be used in the present application, so that multiple sets of artificial chordae tendineae can simultaneously be sutured.

A grasping-feedback device is further used in the present application to determine whether the valve is correctly grasped. Compared to the related arts, the present application can reduce surgical risk and lower the production and research costs.

The above description are exemplarily embodiments of the present application but not considered as limiting the present application. For a person skilled in the art, modifications and changes may be made in the detail. Within the principles of the present disclosure, any modification, equivalent substitution, or change shall be included within the scope of the appended claims.

What is claimed is:

1. A valve repair system for implanting artificial chordae tendineae, comprising:
   a handle operation device at a proximal end;
   a valve clamping device at a distal end;
   at least one set of valve puncturing devices at the distal end;
   a catheter connected between the handle operation device and the valve clamping device; and
   a grasping-feedback device configured to determine whether a valve is correctly grasped, wherein the valve clamping device comprises a clamping mechanism at the distal end and a clamping-control component connected to the clamping mechanism, the clamping-control component configured to control the clamping mechanism to open or close, the clamping-control component is configured to receive the artificial chordae tendineae, the clamping mechanism comprises a proximal clamp and a distal clamp;

wherein each of the at least one set of valve puncturing devices comprises a pulling loop configured to pull the artificial chordae tendineae, a connecting component configured to fix the pulling loop, and a puncture needle assembly, the pulling loop and the connecting component are received in the distal clamp;

the puncture needle assembly comprises a puncture needle and a puncture hollow tube sleeved on the puncture needle, a distal end of the puncture needle assembly is received in the proximal clamp, the puncture hollow tube is detachably connected to the connecting component;

the handle operation device comprises a handle, a puncturing-operation mechanism received in the handle, a clamping-operation mechanism received in the handle, and a feedback-operation mechanism received in the handle, the puncturing-operation mechanism is connected to the puncture needle assembly, the clamping-operation mechanism is connected to the clamping-control component, and the feedback-operation mechanism is connected to the grasping-feedback device.

2. The valve repair system for implanting artificial chordae tendineae according to claim 1, wherein a distal end of the puncture hollow tube comprises a limiting head, the limiting head is configured to limit a length of the puncture needle protruding from the puncture hollow tube, and a taper of a tip at a distal end of the puncture needle is equal to a taper of an outer wall of the limiting head at the distal end of the puncture hollow tube.

3. The valve repair system for implanting artificial chordae tendineae according to claim 1, wherein the connecting component is connected to the puncture hollow tube by screw connection, snap fit, insertion connection, or interference fit.

4. The valve repair system for implanting artificial chordae tendineae according to claim 1, wherein an outer wall of the connecting component is provided with at least one circle of oblique grooves or teeth, an inner wall of the puncture hollow tube is provided with at least one circle of teeth or oblique grooves, the teeth are configured to resist against the oblique grooves to connect the connecting component to the puncture hollow tube.

5. The valve repair system for implanting artificial chordae tendineae according to claim 1, wherein the distal clamp defines a receiving chamber for receiving the pulling loop and the connecting component, one end of the receiving chamber is connected to the clamping-control component, and another end of the receiving chamber extends to a clamping surface of the distal clamp.

6. The valve repair system for implanting artificial chordae tendineae according to claim 1, further comprising a pair of clamping-control components, a pair of valve puncturing devices, and a pair of grasping-feedback devices.

7. The valve repair system for implanting artificial chordae tendineae according to claim 1, wherein the grasping-feedback device comprises a grasping-feedback mechanism and a feedback-control mechanism connected to the grasping-feedback mechanism;

the grasping-feedback mechanism comprises a main feedback component arranged in the proximal clamp and an auxiliary feedback component arranged in the distal clamp, the main feedback component is opposite to the auxiliary feedback component;

the feedback-control mechanism comprises a feedback-control component extending through the catheter, a proximal end of the feedback-control component extends to a proximal end of the catheter and is connected to the feedback-operation mechanism, a distal end of the feedback-control component is connected to the main feedback component and configured to drive the main feedback component to rotate, one of the main feedback component and the auxiliary feedback component is inserted into another of the main feedback component and the auxiliary feedback component, thereby limiting rotation of the main feedback component and the feedback-control component.

8. The valve repair system for implanting artificial chordae tendineae according to claim 7, wherein the distal end of the feedback-control component is elastically connected to the main feedback component and configured to drive the main feedback component to rotate.

9. The valve repair system for implanting artificial chordae tendineae according to claim 7, wherein grasping-feedback device further comprises a connecting assembly connected to a proximal end of the main feedback component, the distal end of the feedback-control component comprises a radial limiting component, the connecting assembly is elastically connected to the radial limiting component to drive the main feedback component to rotate.

10. The valve repair system for implanting artificial chordae tendineae according to claim 9, wherein the connecting assembly comprises a feedback-connecting component arranged on a proximal end of the main feedback component and an elastic component configured to return the main feedback component to its original position after the main feedback component is pressed, the elastic component is sleeved on the feedback-connecting component or the radial limiting component, one of the feedback-connecting component and the radial limiting component is inserted into another of the feedback-connecting component and the radial limiting component, thereby allowing the feedback-connecting component to axially move relative to the radial limiting component, and further allowing the feedback-connecting component to radially rotate together with the radial limiting component.

11. The valve repair system for implanting artificial chordae tendineae according to claim 10, wherein the connecting component and the radial limiting component are connected to each other by key connection, spline connection, resisting connection, or profile connection.

12. The valve repair system for implanting artificial chordae tendineae according to claim 11, wherein the elastic component is a spring or an elastic sleeve.

13. The valve repair system for implanting artificial chordae tendineae according to claim 11, wherein a stopper is provided at a distal end of the feedback-connecting component, two ends of the elastic component are resisted against the stopper and a distal end of the radial limiting component, respectively, and the feedback-connecting component is inserted into the radial limiting component.

14. The valve repair system for implanting artificial chordae tendineae according to claim 11, wherein the radial limiting component comprises a stopper, two ends of the elastic component are resisted against the stopper and a proximal end of the feedback-connecting component, respectively, and the radial limiting component is inserted into the feedback-connecting component.

15. The valve repair system for implanting artificial chordae tendineae according to claim 1, wherein the feedback-operation mechanism comprises a connecting block connected to a proximal end of the feedback-control component, a knob slidably connected to the handle in an axial direction of the handle, and a torsion spring sleeved on the connecting block, the knob is further connected to the connecting block and configured to drive the connecting block to rotate, and the torsion spring is configured to return the connecting block to its original position.

16. The valve repair system for implanting artificial chordae tendineae according to claim 15, wherein the connecting block comprises a shaft and a blade extending from one side of the shaft, the torsion spring is sleeved on the shaft, one end of the torsion spring is fixed to or resisted against a rib inside the handle, and another end of the torsion spring is resisted against or fixed to the blade.

17. The valve repair system for implanting artificial chordae tendineae according to claim 16, wherein the knob comprises a knob body, a curve plate, and a fitting component, the curve plate is between the knob body and the fitting component, the fitting component defines a sliding groove, the blade of the connecting block is inserted into the sliding groove, and the blade is configured to axially slide in the sliding groove.

18. The valve repair system for implanting artificial chordae tendineae according to claim 15, wherein the handle comprises a sliding component, the sliding component defines a limiting groove, and the limiting groove is configured to limit a rotation of the knob.

19. The valve repair system for implanting artificial chordae tendineae according to claim 18, wherein the sliding component further comprises a curve sliding surface, a central axis of the curve sliding surface is aligned with the shaft of the connecting block, the knob is slidably connected to the sliding component, the knob extends through the limiting groove and is connected to the connecting block, and the knob is configured to circumferentially move around the sliding component and drive the connecting block to rotate.

* * * * *